United States Patent [19]

Mullenbach et al.

[11] Patent Number: 5,171,680

[45] Date of Patent: Dec. 15, 1992

[54] SUPEROXIDE DISMUTASE ANALOGS HAVING NOVEL BINDING PROPERTIES

[75] Inventors: Guy T. Mullenbach, Oakland; Robert A. Hallewell; Pablo Valenzuela, both of San Francisco, all of Calif.

[73] Assignee: Chiron Corporation, Emeryville, Calif.

[21] Appl. No.: 561,442

[22] Filed: Aug. 1, 1990

Related U.S. Application Data

[63] Continuation of Ser. No. 206,513, Jun. 14, 1988, abandoned.

[51] Int. Cl.$^5$ ............... C12N 9/02; C12N 1/21; C12N 1/14; C12N 15/53
[52] U.S. Cl. ............... 435/189; 435/252.3; 435/254; 435/320.1; 536/27; 424/94.4
[58] Field of Search .............. 435/189, 320.1, 252.3, 435/254; 424/94.4; 536/27

[56] References Cited

U.S. PATENT DOCUMENTS

| | | | |
|---|---|---|---|
| 4,391,749 | 7/1983 | Ruoslahti et al. | 260/123.7 |
| 4,517,685 | 5/1985 | Ruoslahti et al. | 3/1 |
| 4,578,079 | 3/1986 | Ruoslahti et al. | 623/11 |
| 4,589,881 | 5/1986 | Pierschbacher | 623/11 |
| 4,614,517 | 9/1986 | Ruoslahti et al. | 623/11 |
| 4,661,111 | 4/1987 | Ruoslahti et al. | 623/11 |

FOREIGN PATENT DOCUMENTS

| | | |
|---|---|---|
| 0138111 | 4/1985 | European Pat. Off. . |
| 84/00540 | 2/1985 | PCT Int'l Appl. . |

OTHER PUBLICATIONS

Barra et al., J. Biol. Chem. (1984) 259(20):12595–12601.
Hjalmarsson et al., (1987) Proc. Natl. Acad. Sci., USA 84, 6340–6344.
Santoro, S. A., et al. (1987) Cell 48, 867–873.
Ruoslahti, E. et al. (1986) Cell 44, 517–518.
Pierschabacher, M. D., et al. (1984) Nature 309, 30–33.
Abstract Nos. 564, 1140–1141, 649, 15–17, 715, 901, 908, 1043, 1587 from Thrombosis and Haemostasis 58:Abstract "Eleventh International Congress", Brussels, Belgium, Jul. 1987.
Betsholtz, Nature (1986) 320:695–699.
Bock et al. Biochem. J. (1980) 191:769–776.
Hong et al., Proc. Natl. Acad. Sci. (1987) 84:7962–7966.
Iwamoto, Science (1987) 238:1132–699.
Jabusch et al., Biochemistry (1980) 19:2310–2316.
Kaplan et al., Blood (1979) 53:604–618.
Luster et al., Nature (1985) 315:672–676.
Naccache et al., Science (1979) 203461–463.
Peterson et al., J. Biol. Chem. (1987) 262(17):8061–8065.
Petrone et al., Proc. Natl. Acad. Sci. (1980)77(2):1159–1163.
Pyatak et al., Res. Comm. Chem. Path. & Pharm. (1980) 29:113–120.
Timmons et al., Proc. Natl. Acad. Sci. (1984) 81:4935–4935.
Turrens et al., J. Clin. Invest. (1984) 73:87–95.
Yoshimura et al., Proc. Natl. Acad. Sci. (1987)84:9233–9237.
Zamir et al., Proc. Natl. Acad. Sci. (1987) 84:541–545.
Carlsson et al., Proc. Natl. Acad. Sci. (1981) 78:2403–2406.

(List continued on next page.)

Primary Examiner—Charles L. Patterson, Jr.
Attorney, Agent, or Firm—Morrison & Foerster

[57] ABSTRACT

Superoxide dismutase (SOD) analogs whose amino acid sequence includes a heterologous peptide domain such as the RGDX tetrapeptide found in fibronectin or the LGGAKQAGDV decapeptide found in fibrinogen that enables the analog to bind to a moiety that is normally present at sites of desired SOD therapy. The domain is incorporated into the SOD sequence in a manner in which it is available to interact with such moieties but does not destroy the enzymatic activity of the molecule. The inclusion of the domain enables the analog to more readily access the target tissue upon which it is to act and/or increase the corporeal half-life of the molecule.

7 Claims, 6 Drawing Sheets

OTHER PUBLICATIONS

Daly et al., *Tetrahedron Letters* (1988) 29(46):5859–5862.
Hynes, *Cell* (1987) 48:549–554.
Karlsson et al., *Biochem. J.* (1987) 242:55–59.
Lui et al., *J. Bio. Chem.* (1987) 262(36):17356–17361.
Ny et al., *Proc. Natl. Acad. Sco.* (1984) 81:5355–5359.
Pierschbacher et al., *J. Biol. Chem.* (1982) 257:9593–9597.
Plow et al., *J. Biol. Chem.* (1984) 259:5388–5391.
Ruoslahti et al., *Science* (1987) 238:491–497.
Roberts et al., *J. Biol. Chem.* (1986) 261:6872–6877.
Smith et al., *J. Biol. Chem.* (1987) 262(25):11964–11972.
Pierschbacher, M. D., et al. (1981) Cell 26, 259–267.
Marklund, S. L. (1982) Proc. Natl. Acad. Sci., USA 79, 7634–7638.

MetAlaThrLysAlaValAlaValLeuLysGlyAspGlyProValGlnGlyIleIleAsn

```
CATGGCTACAAAGGCTGTTGCTGTTTTGAAGGGTGACGGGCCCGTTCAAGGTATTATTAAC
CGATGTTTCCGACAACGACAAAACTTCCCACTGCCCGGGCAAGTTCCATAATAATTG
                              ^ApaI
```

PheGluGlnLysGluSerAsnGlyProValLysValTrpGlySerIleLysGlyLeuThr

```
TTCGAGCAGAAGGAAAGTAATGGACCAGTGAAGGTGTGGGGAAGCATTAAAGGACTGACT
AAGCTCGTCTTCCTTTCATTACCTGGTCACTTCCACACCCCTTCGTAATTTCCTGACTGA
```

GluGlyLeuHisGlyPheHisValHisGluPheGlyAspAsnThrAlaGlyCysThrSer

```
GAAGGCCTGCATGGATTCCATGTTCATGAGTTTGGAGATAATACAGCAGGCTGTACCAGT
CTTCCGGACGTACCTAAGGTACAAGTACTCAAACCTCTATTATGTCGTCCGACATGGTCA
   ^StuI
```

AlaGlyProHisPheAsnProLeuSerArgLysHisGlyGlyProLysAspGluGluArg

```
GCAGGTCCTCACTTTAATCCTCTCTCGAGAAAACACGGTGGGCCAAAGGATGAAGAGAGG
CGTCCAGGAGTGAAATTAGGAGAGAGCTCTTTTGTGCCACCCGGTTTCCTACTTCTCTCC
```

HisValGlyAspLeuGlyAsnValThrAlaAspLysAspGlyValAlaAspValSerIle

```
CATGTTGGAGACTTGGGCAATGTGACCGCGGACAAAGATGGTGTGGCCGATGTATCGATT
GTACAACCTCTGAACCCGTTACACTGGCGCCTGTTTCTACCACACCGGCTACATAGCTAA
```

GluAspSerValIleSerLeuSerGlyAspHisSerIleIleGlyArgThrLeuValVal

```
GAAGATTCTGTGATATCACTCTCAGGAGACCATTCCATCATTGGCCGCACACTAGTGGTC
CTTCTAAGACACTATAGTGAGAGTCCTCTGGTAAGGTAGTAACCGGCGTGTGATCACCAG
```

HisGluLysAlaAspAspLeuGlyLysGlyGlyAsnGluGluSerThrLysThrGlyAsn

```
CATGAAAAAGCAGATGACTTGGGCAAAGGTGGAAATGAAGAAAGTACAAAGACAGGAAAC
GTACTTTTTCGTCTACTGAACCCGTTTCCACCTTTACTTCTTTCATGTTTCTGTCCTTTG
```

AlaGlySerArgLeuAlaCysGlyValIleGlyIleAlaGlnOC

```
GCTGGATCCCGTTTGGCTTGTGGTGTAATTGGGATCGCCCAATAAG
CGACCTAGGGCAAACCGAACACCACATTAACCCTAGCGGGTTATTCAGCT
   ^BamHI
```

```
        GlyProValGlnGlyIleIleAsnPheGluGlnArgGlyAspThrValLysValTrpGly
    5'    CGTTCAAGGTATTATTAACTTCGAGCAGAGAGGTGACACCGTGAAGGTGTGGGGA
    3'    CCGGGCAAGTTCCATAATAATTGAAGCTCGTCTCTCCACTGTGGCACTTCCACACCCCT

SerIleLysGlyLeuThrGluGly

AGCATTAAAGGACTGACTGAAGG    3'        T-2(u)(78)
    TCGTAATTTCCTGACTGACTTCC    5'        T-2(l)(82)
```

FIG. 4

```
        GlySerArgLeuAlaCysGlyValIleGlyIleAlaGlnGlyGlnGlnHisHisLeuGly
    5'    GATCCCGTTTGGCTTGTGGTGTAATTGGGATCGCCCAAGGTCAACAACACCACTTGGGT
    3'    GGCAAACCGAACACCACATTAACCCTAGCGGGTTCCAGTTGTTGTGGTGAACCCA

GlyAlaLysGlnAlaGlyAspVal0C

GGTGCTAAGCAAGCTGGTGACGTTTAAG        3'        T-8(u)(87)
    CCACGATTCGTTCGACCACTGCAAATTCAGCT    5'        T-8(l)(87)
```

SUPEROXIDE DISMUTASE ANALOGS HAVING NOVEL BINDING PROPERTIES

This application is a continuation of application Ser. No. 07/206,513 filed, Jun. 14, 1988 now abandoned.

TECHNICAL FIELD

This invention is in the fields of protein chemistry, genetic engineering, and pharmaceuticals. More particularly, it relates to superoxide dismutase (SOD) analogs that are modified in a manner in which they have binding properties that enable them to be localized at sites where superoxide dismutase therapy is required and/or extend their corporeal lifetimes.

BACKGROUND ART

SODs are a family of enzymes that catalyze the destruction of superoxide ions. SODs are metalloproteins that are individually characterized by their respective metal ions—which can be iron, manganese, or copper metal ions and zinc. The ability of SODs to catalyze the destruction of superoxide ions renders them useful in a variety of therapeutic settings such as in reducing reperfusion injury and in treating inflammation. The amino acid sequence of human Cu/Zn SOD is described in Jabusch et al, Biochemistry (1980) 19:2310-2316. The cloning and sequencing of human Cu/Zn SOD and the production of human Cu/Zn SOD in bacteria and yeast are described in EPA 84111416.8 (published Apr. 24, 1985 under number 0138111). Human Cu/Zn SOD is normally a homodimer of two chains bound together by hydrophobic interaction. The homodimer has a molecular weight of approximately 32 kd.

The primary structure of human Mn SOD is described by Barra et al, J.B.C. (1984) 259:12595-12601. The cloning and sequencing of human Mn SOD and the production of human Mn SOD in yeast is described in copending U.S. application Ser. No. 918,534, filed Oct. 14, 1986.

In achieving its therapeutic potential SOD must (1) achieve access to the target tissue upon which it is to act (2) maintain its molecular integrity while in transit and at the site of action and (3) not be cleared too rapidly from circulation. Prior modifications of SOD have focused on only the latter two of these requirements. For example, commonly owned copending U.S. application Ser. No. 026,143, filed Mar. 16, 1987 describes SOD polymers composed of covalently coupled SOD dimers which are not cleared as rapidly from circulation as native SOD. Res Commun. in Chem. Path. & Pharmacol. (1980) 29:113-120 and Proc. Nat'l Acad. Sci. U.S.A. (1980) 77:1159-1163 describe conjugates of SOD and macromolecules such as polyethylene glycol that also have increased circulatory half-lives relative to wild-type SOD. J. Clin. Invest. (1984) 73:87-95 describes SOD encapsulated in liposomes to protect the SOD from proteolysis and extend its clearance time.

In contrast, the present invention is primarily directed to modifying SOD in a manner to enable it to more readily access the target tissue upon which it is to act and/or to extend its corporeal lifetime. This is achieved by modifying the amino acid sequence of SOD to include a heterologous peptide domain that binds to a moiety that localizes at the site where the superoxide dismutase therapy is desired or binds to the site itself. Such domains are sometimes referred to as "adhesive peptide signals" herein.

Prior workers have identified adhesive peptide signals of various proteins that bind to cells, bodies, or molecules that are real to or commonly localize at sites at which SOD therapy may be desirable. The signals for fibrinogen, fibronectin, and von Willebrand factor are described in Nature (1984) 309:30-33; Proc. Nat'l Acad. Sci. U.S.A. (1984) 81:4935-4939; Cell (1986) 44:517-518 and Cell (1987) 48:867-873. Signals for laminin are described in Science 1987) 238:1132, for extracellular superoxide dismutase (EC-SOD) in PNAS (1987) 84:6340, for platelet-derived growth factor (PDGF) in Nature (1986) 320:695, for tissue plasminogen activator (tPA) in Abstracts 1141, 1144, 1043, and 1587 in "Thrombosis and Haemostasis, Volume 58, Abstracts", Eleventh International Congress, Brussels, Belgium, July 1987, and chemotactic factor in PNAS (1987) 84:9233. Those for Antithrombin III are described in Abstracts 543-545, ibid, and in J. Biol. Chem. (1987) 262:8061, 11964, 17356. The adhesive peptide signals for antiplatelet GPIIb/IIIa receptor and anti-endothelial cell GPIIb/IIIa receptor antibodies are discussed in Abstracts 15, 715, 901 and 908 of "Thrombosis and Haemostasis, Volume 58, Abstracts", supra. Those for vitronectin appear in Abstracts 15-17 and 564, ibid., for urokinase in Abstract 1140, ibid., for thrombin inhibitor in Abstract 649, ibid. The signal for chemotactic inhibitor is disclosed in Science (1979) 203:461, and for chemotactic agonists in PNAS (1987) 84:7964. The signals for platelet factor-4 appear in Blood (1979) 53:604 and Biochem. J. (1980) 191:769 and those for Gamma IP10 in Nature (1985) 315:672.

Applicants are unaware of any prior efforts to incorporate any of these adhesive domains or signals into other polypeptides to impart binding activity thereto.

DISCLOSURE OF THE INVENTION

One aspect of this invention is a SOD analog having dismutase activity and whose amino acid sequence includes a heterologous peptide domain that provides the analog with an ability to bind to a moiety that localizes at or is local to a body site at which SOD therapy is desired.

DNA sequences encoding such SOD analogs, expression vectors containing such DNA sequences, cells transformed with such vectors, and processes for making the analogs by growing such transformed cells are another aspect of the invention.

Still other aspects of the invention are pharmaceutical compositions which contain the analogs and therapeutic methods which employ the analogs.

MODES FOR CARRYING OUT THE INVENTION

A. Definitions

The term "SOD" intends a polypeptide having the amino acid sequence of a native intracellular superoxide dismutase and fragments, analogs, or muteins thereof having substantially homologous amino acid sequences thereto which may differ in one or more amino acid substitutions, additions or deletions (other than those directed by the present invention) but still retain the enzymatic activity of the native superoxide dismutase. Examples of such analogs are those described in commonly owned copending U.S. application Ser. No. 003578, filed Jan. 15, 1987. Polymers of SOD, such as those described in said U.S. Ser. No. 026,143, the disclosure of which is incorporated herein by reference, are intended to be included within the term. The term also encompasses SOD of various mammalian species. Human SOD is preferred for use in humans. Human Cu/Zn SOD and human Mn SOD are preferred species of SOD for modification in accordance with the present invention. The term "substantially homologous", as used above, intends at least about 75% identity, more usually at least about 85% identity, in amino acid sequence.

A "replicon" is any genetic element (e.g., a plasmid, a chromosome, a virus) that behaves as an autonomous unit of polynucleotide replication within a cell; i.e., capable of replication under its own control.

A "vector" is a replicon in which another polynucleotide segment is attached, so as to bring about the replication and/or expression of the attached segment. An "expression vector" refers to a vector capable of autonomous replication or integration and contains control sequences which direct the transcription and translation of the SOD analog DNA in an appropriate host.

A "coding sequence" is a polynucleotide sequence which is transcribed and/or translated into a polypeptide.

A "promoter sequence" is a DNA regulatory region capable of binding RNA polymerase and initiating transcription of a downstream (i.e., in the 3' direction) coding sequence.

A coding sequence is "under the control" of the promoter sequence in a cell when transcription of the coding sequence results from the binding of RNA polymerase to the promoter sequence; translation of the resulting mRNA then results in the polypeptide encoded within the coding sequence.

"Operably linked" refers to a juxtaposition wherein the components are configured so as to perform their usual function. Thus, control sequences operably linked to a coding sequence are capable of effecting the expression of the coding sequence.

"Control sequences" refers to those sequences which control the transcription and/or translation of the coding sequence(s); these may include, but are not limited to, promoter sequences, transcriptional initiation and termination sequences, and translational initiation and termination sequences. In addition, "control sequences" refers to sequences which control the processing of the polypeptide encoded within the coding sequence; these may include, but are not limited to sequences controlling secretion, protease cleavage, and glycosylation of the polypeptide.

"Transformation" is the insertion of an exogenous polynucleotide into a host cell. The exogenous polynucleotide may be maintained as a plasmid, or alternatively, may be integrated within the host genome.

B. Characterization of SOD Analogs

The amino acid sequence of the SOD analogs of this invention comprise the amino acid sequence of SOD altered via amino acid substitution, deletion, addition, or combinations thereof to include one or more heterologous peptide domains that provide the analog with the ability to bind to a moiety that localizes at or is local to a body site (e.g., the endothelial wall to which a hemostatic fibrin plug adheres) at which SOD therapy is desired. The binding activity of these analogs lessens the likelihood of their being cleared from circulation. Accordingly the corporeal half-lives of the analogs will typically be greater than native SOD and the concentration of analog at the desired site maintained at higher levels relative to native SOD.

The moiety to which the analog is capable of binding via the domain(s) depends upon the nature of the domains and maybe, for example, cells such as phagocytes (macrophages, neutrophils), fibroblasts and endothelial cells, noncellular bodies such as platelets, or other proteinaceous or nonproteinaceous molecules such as glycosaminoglycans (heparin), fibrin, and thrombin. In some instances these moieties localize at sites of desired SOD therapy (e.g., platelets, neutrophils) or are cells that are local to such a site (e.g., endothelial cells).

The nature and location of the alteration is such that the domain(s) is(are) available to interact with and bind to such moieties but not destroy the superoxide dismutase activity of the analog. Accordingly, the domains will be positioned at a location that is exposed in the tertiary structure of native SOD, such as a hydrophilic loop or the amino or carboxy termini, and their size, charge, hydrophilicity/hydrophobicity, will be such as to not alter the molecule (e.g., by changing its tertiary structure or charge distribution) in a manner that eliminates superoxide dismutase activity. The domain may include innocuous additional amino acid modifications beyond those that are crucial for binding activity. These additional modifications may serve a spacer function or otherwise serve to enhance the accessibility of the domain to the moiety or maintain the enzymatic activity of the analog. Normally the number of amino acid alterations directed by the invention will not exceed about 40, usually not more than about 30, and preferably not more than about 20.

Representative domains are those described in the Background section, supra. In addition, suitable domains that provide binding activity may be identified by making random amino acid alterations at selected sites (e.g, the hydrophilic loops or amino or carboxy termini) in the native SOD sequence and then screening the resulting analogs for enzymatic activity and binding activity. Preferred domains are the RGDX tetrapeptide (Nature (1984) 309:30 and U.S. Pat. No. 4,578,079), the RGDX tetrapeptide with up to about a total of 15 to 20 flanking residues (on the carboxy and/or amino terminal side of the tetrapeptide), the decapeptide LGGAKQAGDV which is found at the carboxy terminus of fibrinogen, and that decapeptide with up to a total of about 10 flanking residues (on the carboxy and/or amino terminal side) of the decapeptide found in the native fibrinogen sequence. "X" in RGDX represents an amino acid that does not eliminate the binding properties of the domain.

It should be appreciated that many of the possible analogs that may be made by incorporating the domains described in the Background section into SOD or by making random alterations in the SOD sequence will either lack enzymatic activity and/or lack the desired binding activity and thus not be within the invention. Those analogs falling within the invention may be identified by routine screening for enzymatic activity and binding activity. Enzymatic activity may be assayed by the pyrogallol assay and binding activity (depending upon the target moiety) according to the various art assays used to identify the domains described in the Background section (e.g., PNAS (1981) 78:2403-2406 and Nature (1984) 309:30-33).

The N-terminus of the analog may be acetylated (as in native human Cu/Zn SOD) or lack acetylation depending upon the organism in which the analog is produced. Bacterially produced analog will lack such acetylation whereas analog produced in yeast using the procedures described in EPA 0138111 are so acetylated. Analogs made in mammalian cells will also be acetylated. Analogs having such acetylation are preferred. Similarly, the analog may be glycosylated or unglycosylated depending upon the organism and signaling sequence with which it is produced.

C. Synthesis of SOD Analogs

Figure 1:
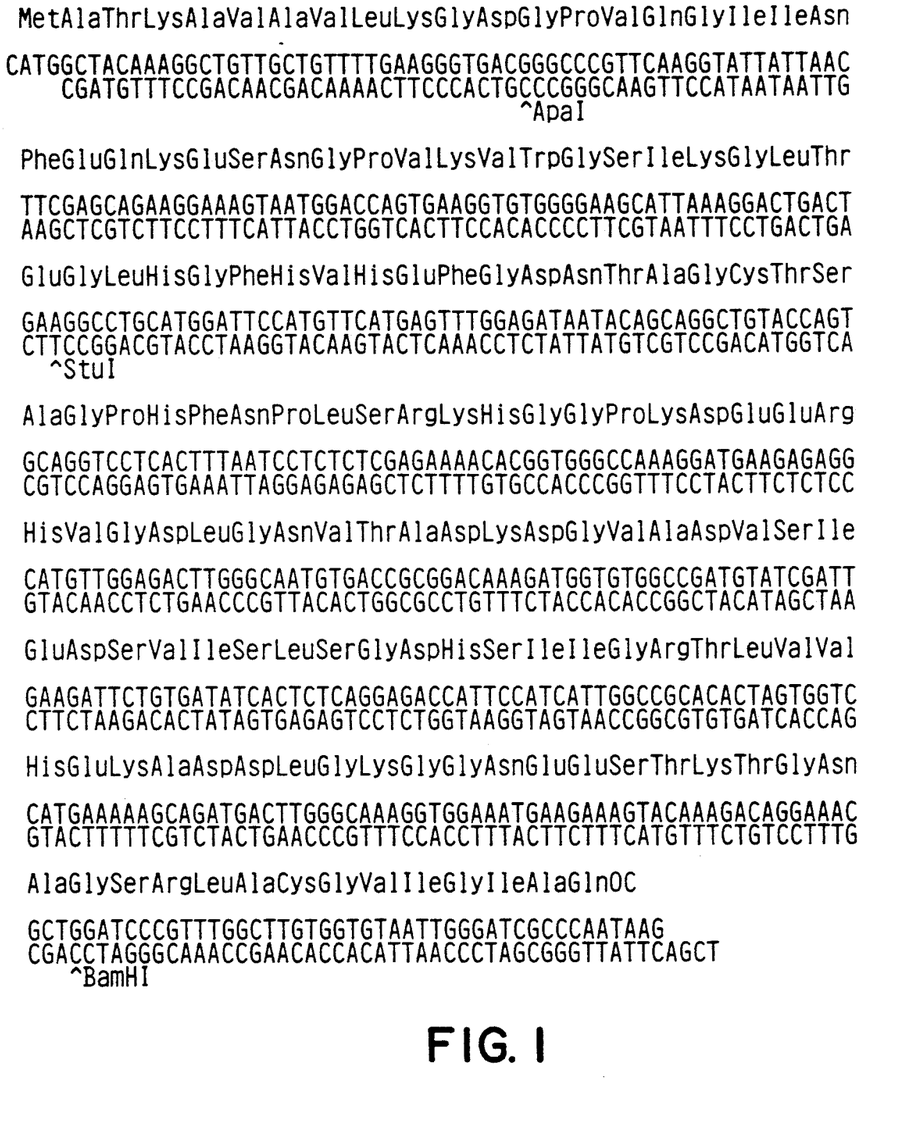
FIG. 1 is the nucleotide sequence of a partially synthetic human Cu/Zn SOD cDNA and the deduced amino acid sequence of human Cu/Zn SOD.

Genes encoding the analogs of human Cu/Zn SOD may be made via oligonucleotide synthesis and ligation, site directed mutagenesis of the DNA sequences shown in FIG. 1 and/or by insertion of synthetic DNA fragments that encode the desired amino acid modifications into a DNA sequence encoding human Cu/Zn SOD. Genes encoding analogs of other SODs, such as Mn SOD, may be made by similar procedures. Site directed mutagenesis techniques are well known in the art. See for instance, Smith and Gilliam in Genetic Engineering Principles and Methods, Plenum press (1981) 3:1-32; Zoller and Smith, Nucleic Acids Res. (1982) 10:6487-6500; and Brake et al, Proc. Natl. Acad. Sci. U.S.A. (1984) 81:4642-4646. The mutant genes may be inserted into suitable prokaryotic or eukaryotic vectors, the resulting expression vectors incorporated into suitable host organisms or cells, the recombinant organism or cell grown under conditions that result in expression of the mutant gene, and the resulting analog isolated from the host or, if secreted, from the growth medium using the same techniques as are described in said EPA 0138111 to produce recombinant human Cu/Zn SOD. The disclosure of that EPA is incorporated herein by reference. The metal ions required for enzymatic activity may be provided by growing the recombinant hosts in medium supplemented with the ion(s) or by dialyzing a solution of the analog against a solution containing the ions.

In creating an expression vector, the mutant sequence is located in the vector with the appropriate control DNA sequences, which include a promoter, a ribosomal binding site, and transcriptional and translational stop codons. The positioning and orientation of the coding sequence with respect to the control sequences is such that the coding sequence is transcribed under the control of the control sequences. In addition to control sequence, it may be desirable to add regulatory sequences which allow for regulation of the expression of the hSOD analog gene relative to the growth of the host cell.

D. Formulation and Use of SOD Analogs

The SOD analogs of the invention may be used for the same purposes as SOD. The analogs may be used in human or veterinary medicine to treat (i.e., cure, alleviate or prevent) a variety of conditions. They are useful as antiinflammatory agents, chemopreventive agents to prevent oncogenesis and tumor promotion, protective agents to reduce cytotoxic and cardiotoxic effects of anticancer drugs or protect ischemic tissue. The treatment of medical conditions with SOD is referred to as "SOD therapy" Like native SOD, the analogs catalyze the dismutation of superoxide radicals to hydrogen peroxide and molecular oxygen and may thus be used to reduce perfusion injury following ischemia, prolong the viability of excised isolated organ transplants, reduce injury on reperfusion following organ transplant or spinal cord ischemia, reduce cardiac infarct size, reduce spinal cord injury and treat bronchial pulmonary dysplasia.

For therapeutic medical applications the analogs may be administered orally or parenterally to individuals in various dosage forms such as tablets, capsules and injectables. When used to treat tissues in vitro the analog will be added to the perfusion or culture medium. The analog may be administered neat or admixed in effective amounts with pharmaceutically acceptable solid, semi-solid or liquid vehicles such as albumins, globulins, dextran, Ficoll polymers, sugars, starches and liposomes. Preferably the SOD analog is conveniently stored lyophilized with sugar, usually sucrose, usually in a ratio of 1:2 w/w. The lyophilized enzyme is conveniently reconstituted in a suitable diluent for the particular application. For example, to treat inflammatory joint disease the SOD analog may be reconstituted in physiologic saline in a volume convenient for intraarticular administration.

The dose of SOD analog administered to an individual will depend upon the nature of the individual being treated, the mode of treatment and the condition being treated. In general the amount administered must be sufficient to provide an enzymatically effective amount of the mutein at the desired site of treatment. In this regard, when the analog is administered systemically, larger doses will typically be required than when the analog is administered locally at the site that requires treatment. By way of example, human patients having inflammatory joint disease are treated by a weekly intraarticular injection into a joint afflicted with the disease of a solution having SOD analog in a suitable diluent in an amount effective to reduce inflammation, usually 1 to 10 mg, more usually 2 to 6 mg. The injections are given weekly for a period of time sufficient to reduce inflammation, usually for 2 to 8 weeks, more usually for 4 to 6 weeks. When used to minimize post-ischemic tissue damage the human patient is administered 10 mg to 1,000 mg, more usually 50 mg to 500 mg of SOD analog in a suitable diluent during the ischemic reaction. When the patient suffers ischemia due to a disease the solution is administered intravenously or intraarterially as a bolus dosage or a continuous infusion. In such situations, the SOD analog may be administered in conjunction with fibrinolytic agents such as urokinase, streptokinase or tissue plasminogen activator (tPA). When ischemia damage is due to a surgical procedure, SOD analog is administered during surgery. This application finds particular use in organ transplant surgery where SOD is preferably administered prior to reirrigation of the organ and is also useful in any other surgery where bloodflow to an organ is interrupted, such as open heart surgery.

F. Examples

The invention is further exemplified by the following examples. These examples are not intended to limit the invention in any manner.

EXAMPLE 1: CONSTRUCTION OF EXPRESSION VECTORS FOR PRODUCING SOD-AS-T-2

Figure 2:
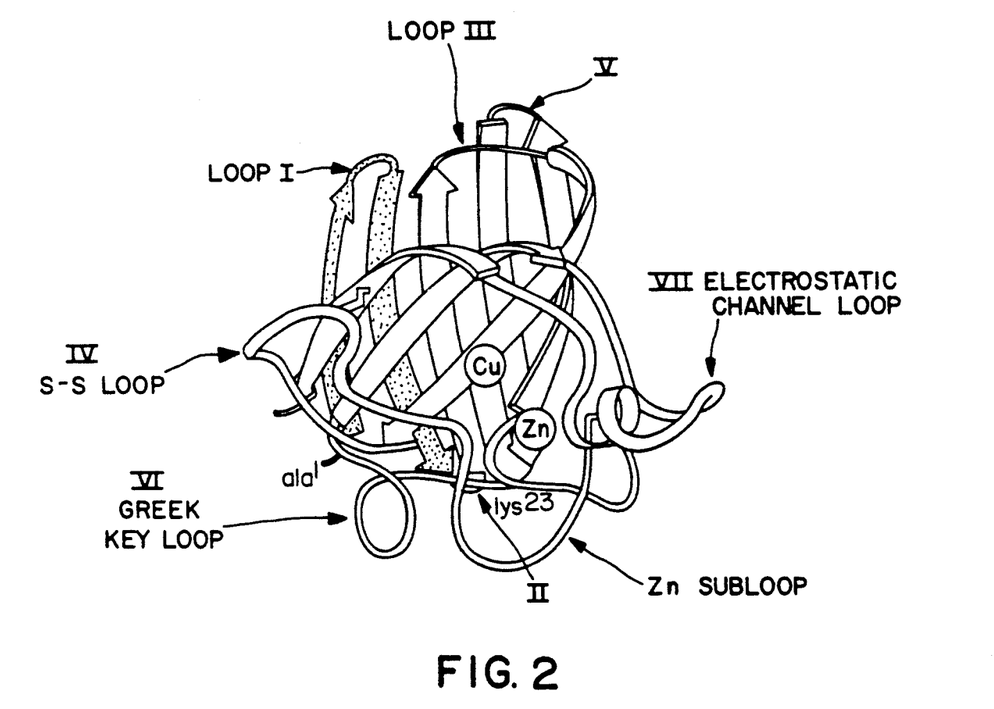
FIG. 2 is a schematic illustration of the tertiary structure of human Cu/Zn SOD.

This example describes the construction of expression vectors for producing a SOD analog that has four amino acid substitutions located in loop II and two amino acid deletions (see FIG. 2). The substitutions were as follows (single letter residue designations followed by residue position number (native Cu/Zn numbering); - indicates a deletion).

| Native Sequence | K23 | E24 | S25 | N26 | G27 | P28 |
|---|---|---|---|---|---|---|
| Analog Sequence | R | G | D | — | — | T |

The analog is designated SOD-AS-T-2 and the bacterial and yeast expression vectors used to produce the analog are designated pSOD-AS-T-2 and pYSOD-AS-T-2 respectively.

Figure 3:
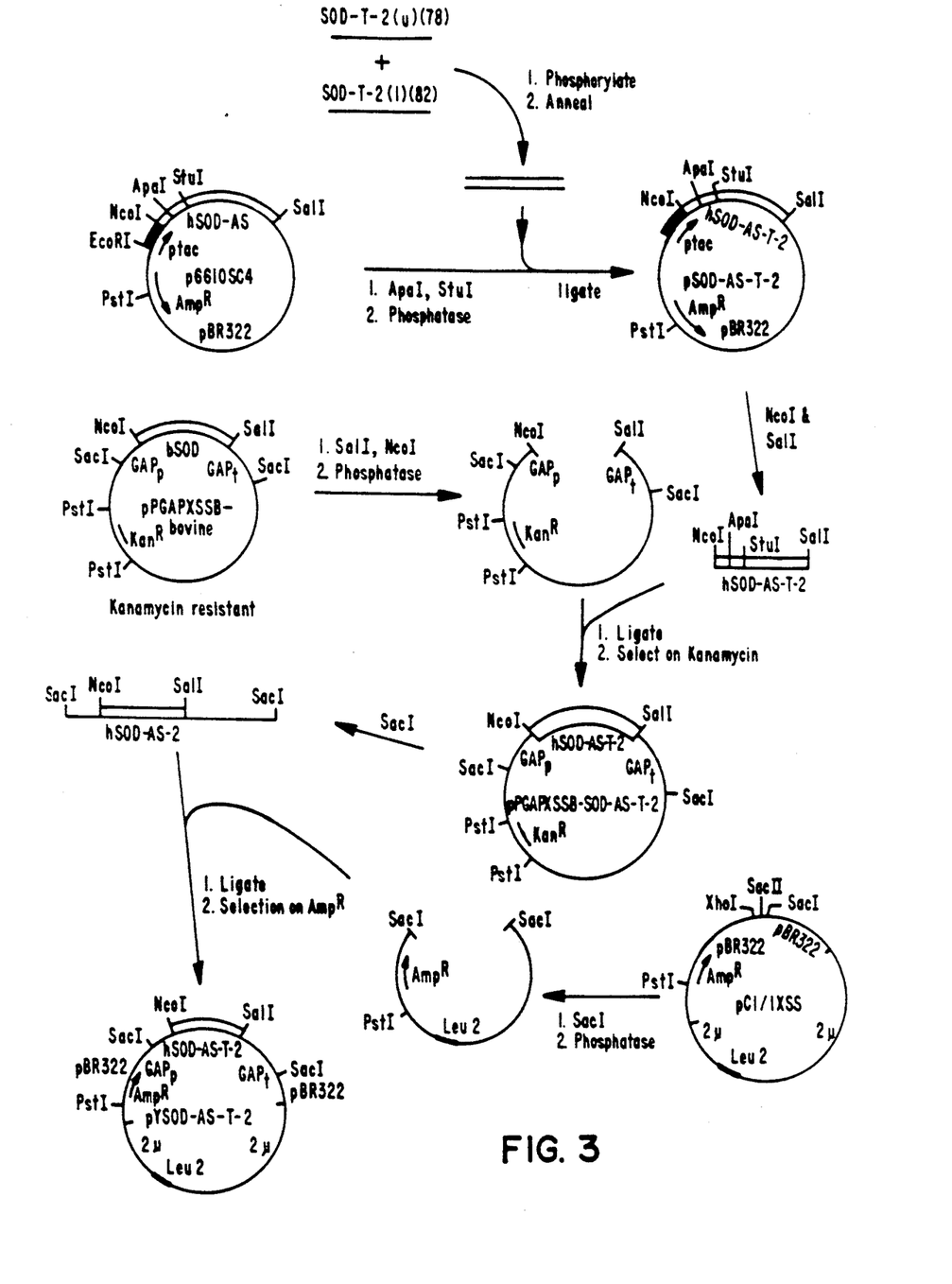
FIG. 3 is a flow diagram depicting the scheme used to construct the yeast expression vector pYSOD-AS-T-2.
Figure 4:
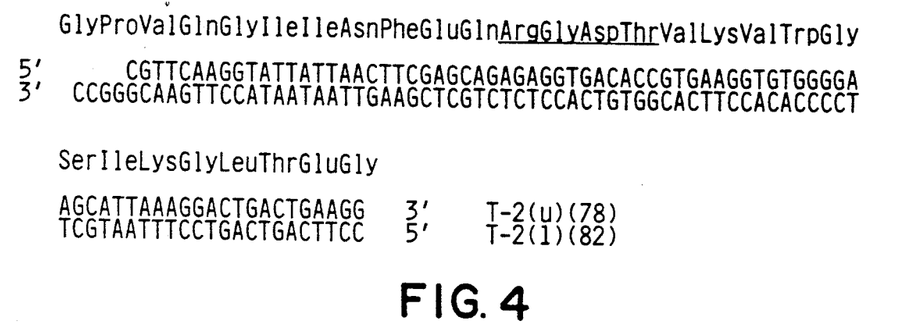
FIG. 4 shows the DNA sequence of the insert used in the construction of pYSOD-AS-T-2.

The constructions of plasmids pSOD-AS-T-2 and pYSOD-AS-T-2 are depicted in FIG. 3. The ampicillin-resistant plasmid p6610SC4 is prepared by inserting the gene segment shown in FIG. 1 between the NcoI and SalI sites of plasmid pNco5AHSODm, which is described in commonly owned copending U.S. patent application Ser. No. 918,534, filed Oct. 14, 1986, the disclosure of which is incorporated herein by reference. A synthetic gene segment (FIG. 4) prepared from synthetic oligomers designated T-2(u)(78) and T-2(1)(82) by phosphorylating individual oligomers and annealing them (by slow cooling of an equimolar solution from 70° to 25° C.), was inserted between the ApaI and StuI sites of p6610SC4 to yield plasmid pSOD-AS-T-2. Plasmid pSOD-AS-T-2 was then treated with NcoI and SalI and the resulting digest was ligated with the kanamycin-resistant, ampicillin-sensitive vector, pPGAPXSSB-bovine which had been digested with NcoI and SalI and treated with alkaline phosphatase. Following ligation and transformation, plasmid pPGAPXSSB-SOD-AS-T-2 was selected on kanamycin. (The construction of pPGAPXSSB-bovine used above had been prepared previously as follows: between the NcoI and SalI sites of pPGAPXSSHSODm [described in said U.S. Ser. No. 918,534] was inserted a segment encoding bovine Cu/Zn SOD. Kanamycin resistance was then conferred by inserting at the PstI site the approximately 1200 bp fragment carrying the kanamycin-resistance element obtained from a PstI digest of PUC-4K [Pharmacia]). A SacI digest of pPGAPXSSB-SOD-AS-T-2 was then ligated with a phosphatase-treated SacI digest of the ampicillin-resistant vector pCl/1XSS (described in said U.S. Ser. No. 918,534).

The resulting plasmid, pYSOD-AS-T-2, was selected on ampicillin.

EXAMPLE 2: CONSTRUCTION OF EXPRESSION VECTORS FOR PRODUCING SOD-AS-T-8

This example describes the preparation of expression vectors for producing a SOD analog that has a C-terminal fibrinogen adhesive domain extension. The sequence of the extension was as follows:

| Native Sequence | G150 | I151 | A152 | Q153 | |
|---|---|---|---|---|---|
| Analog Sequence | G | I | A | Q | GQQHHLGGAKQAGDV |

In the extension GQQHH is a fibrinogen-derived spacer sequence and the remaining decapeptide is the adhesive domain.

This analog is designated SOD-AS-T-8 and the expression plasmids used to produce it are designated pSOD-AS-T-8 for bacteria and pYSOD-AS-T-8 for yeast.

Figure 5:
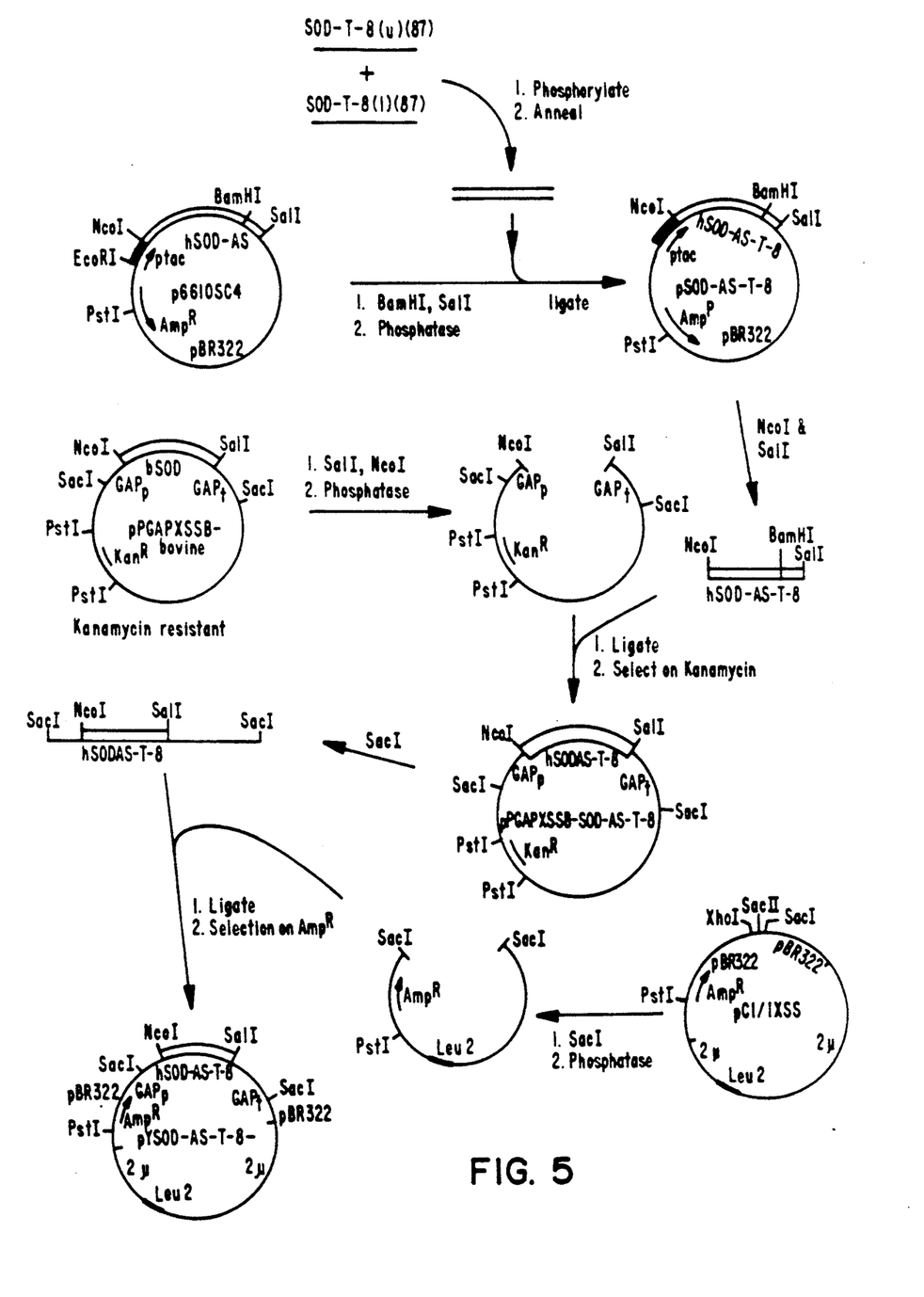
FIG. 5 is a flow diagram depicting the scheme used to construct the yeast expression vector pYSOD-AS-T-8.
Figure 6:
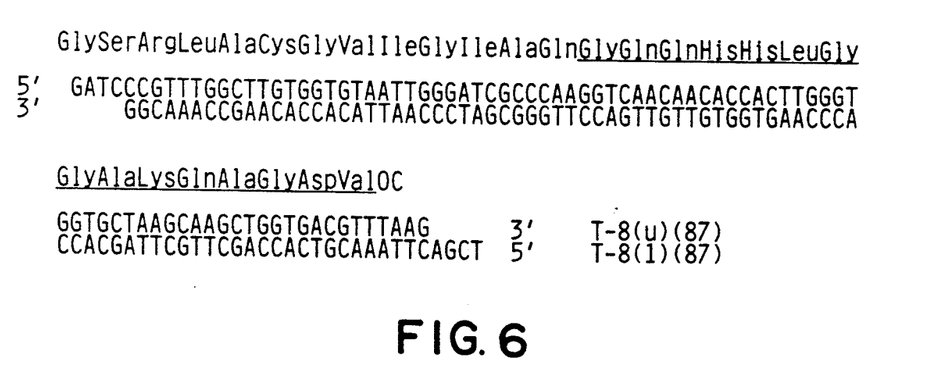
FIG. 6 shows the DNA sequence of an insert used in the construction of pYSOD-AS-T-8.
Figure 7:
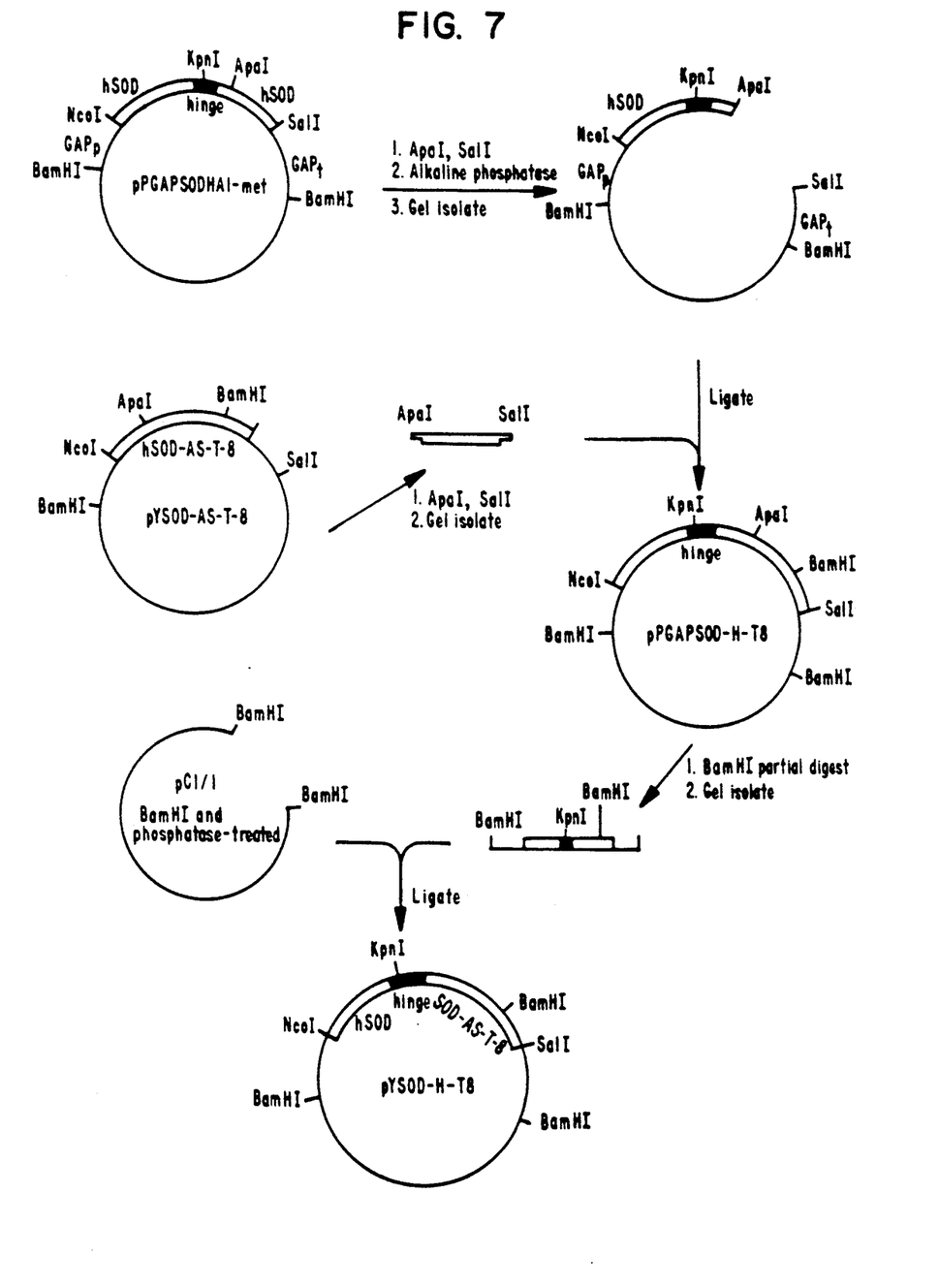
FIG. 7 is a flow diagram depicting the scheme used to construct the yeast expression vector pYSOD-H-T8.

The construction of plasmid pYSOD-AS-T-8 is depicted in FIG. 5. A gene segment (FIG. 6) prepared from synthetic oligomers designated T-8(u)(87) and T-8(1)(87) by phosphorylating individual oligomers and annealing them (by slow cooling of an equimolar solution from 70° to 25° C.), was inserted between the BamHI and SalI sites of p6610SC4 to yield plasmid pSOD-AS-T-8. Plasmid pSOD-AS-T-8 was then treated with NcoI and SalI and the resulting digest was ligated with the kanamycin-resistant, ampicillin-sensitive vector, pPGAPXSSB-bovine, which had first been treated with NcoI and SalI and the alkaline phosphatase. Following transformation, plasmid pPGAPXSSB-SOD-AS-T-8 was selected on kanamycin. A SacI digest of pPGAPXSSB-SOD-AS-T-8 was then ligated with phosphatase-treated SacI digest of the ampicillin-resistant vector, pCl/1XSS. The resulting plasmid pYSOD-AS-T-8 was selected on ampicillin.

EXAMPLE 3: CONSTRUCTION OF EXPRESSION VECTOR FOR PRODUCING SOD-H-T8

This example describes the preparation of a yeast expression vector for producing an analog of a SOD polymer that has the fibrinogen adhesive domain extension described in Example 2. This analog is designated SOD-H-T8 and the expression plasmid used to produce it is designated pYSOD-H-T8.

Plasmid pPGAPSODHA1-met (described in U.S. patent application Ser. No. 026,143, filed Mar. 16, 1987), was digested with ApaI and SalI and then treated with alkaline phosphatase. The larger vector fragment was then gel-isolated. Also prepared was an ApaI-SalI cassette, carrying a portion of the gene coding hSOD-AS-T-8, by digestion of pYSOD-AS-T-8 with ApaI and SalI, followed by gel-isolation of the ca. 500 bp fragment. This fragment was cloned into the vector described above to yield pPGAPSOD-H-T8. Plasmid pPGAPSOD-H-T8 was then partially digested with BamHI and the ca. 2443 bp gel-isolated fragment was cloned into a vector which had been derived from pCl/1 by BamHI digestion and treatment with alkaline phosphatase. Plasmid pYSOD-H-T8 was obtained.

EXAMPLE 4: EXPRESSION OF SOD-AS-T2, SOD-AS-T-8 AND SOD-H-T8

E. coli strain MC1061 was transformed with plasmids pSOD-AS-T-2 or pSOD-AS-T-8 and selected on ampicillin. Transformants were then grown overnight at 37° C. in 1.5 ml of L-broth containing 100 mg/ml of ampicillin and 1.0 mM CuSO$_4$. To the cell pellet obtained by centrifugation was then added 60 ul of lysis buffer (50 mM Tris, pH 8.0, 1.0 mM phenylmethylsulfonyl fluoride, 2.0 mM CuSO₄) and 50 ul of glass beads. The mixture was vortexed 10 sec and shaken (30 min, Eppendorf Mixer 5432). Twenty ul of the supernatant obtained by centrifugation (7 min) was mixed with 7 ul of 6×sample buffer (30% glycerol and dyes), loaded on a 10% polyacrylamide gel and electrophoresed. Gel staining for enzymatic activity was then performed according to Beauchamp and Fridovich (Analyt. Biochem. (1971) 44:276-187). Both are active.

S. cerevesiae, strain PO17, was transformed with pYSOD-AS-T-2, pYSOD-AS-T-8 or pYSOD-H-T8. Transformants were grown and assayed for intracellular recombinant SOD activity as described in EPA 0138111. Each analog exhibited enzymatic activity.

Ten liters of cell culture of the above yeast transformants were grown. Cells were lysed, and SOD-AS-T-2, SOD-AS-T-8 and SOD-H-T8 were purified as described for recombinant Cu/Zn SOD in said EPA 0131811.

EXAMPLE 5: IN VITRO PLATELET BINDING ASSAY

The ability of an analog to bind to platelets may be determined as follows. Three-tenths mg to 30 mg of test SOD analog or rhSOD (recombinant human Cu/Zn SOD) is added to 1.0 ml of heparinized or unheparinized blood and to 1.0 ml of plasma fractions prepared from heparinized and unheparinized blood. After 15 min incubation, the whole blood is centrifuged and SOD activity of the supernatant is determined (pyrogallol assay). Enzymatic activity is also determined for plasma fractions to which SOD or its analogs is similarly added. A decrease in the ratio of enzymatic activity in the whole blood supernatant vs treated plasma compared to the ratio derived from rhSOD-treated fractions (i.e., the control) reflects an increase in platelet binding of the test analog over that of rhSOD.

In preliminary tests using this technique, SOD-AS-T-2 exhibited a decrease in said ratio relative to rhSOD, whereas SOD-AS-T-8 exhibited a ratio approximately the same as rhSOD.

In addition to SOD-AS-T-2, SOD-AS-T-8, and SOD-H-T8 applicants have attempted to prepare or have prepared other SOD analogs in bacteria that included adhesive peptide signals but did not exhibit enzymatic activity. Some of these analogs are reported in the table below.

| Modification Location | Sequence | | | | | |
|---|---|---|---|---|---|---|
| Loop III | | | | | | |
| Wild: | G37 | L38 | T39 | E40 | G41 | L42 |
| Analog: | | | RGD | | (fibronectin insertion) | |
| Analog: | | | GRGDS | | (fibronectin insertion) | |
| Greek key Loop | | | | | | |
| Wild: | L106 | S107 | G108 | D109 | H110 | C111 |
| Analog: | | R | | | | |
| C-Terminus | | | | | | |
| Wild: | G150 | I151 | A152 | Q153 | | |
| Analog: | " | " | " | " | GQQHHL-GYAVTGRGDSPASSKPIS | |
| | | | | (fibronectin extension using its GRGDS complete loop and a tolerated fibrinogen spacer) | | |
| C-Terminus | | | | | | |
| Wild: | G150 | I151 | A152 | Q153 | | |
| Analog: | " | V | C | G | PGLWERQAREHSERKKRRRESECKAA | |
| | | (C-terminal extension with EC-SOD tail and 3 "internal" Cu/Zn SOD residues altered) | | | | |
| Analog: | " | I | A | Q | GQQHHLCVVGVCGPGLWERQAR-EHSERKKRRRESECKAA | |
| | | (a longer EC-SOD tail including all 3 Cys with a fibrinogen spacer; "internal" amino acids unaltered) | | | | |

Modifications of the above-described modes for carrying out the invention that are obvious to those of skill in the fields of protein chemistry, genetic engineering, pharmaceuticals, medicine and related fields are intended to be within the scope of the following claims.

We claim:

1. A superoxide dismutase analog having dismutase activity wherein the superoxide dismutase is human Cu/Zn superoxide dismutase, whose amino acid sequence includes a heterologous peptide domain that comprises a RGDX tetrapeptide, said domain providing the analog with an ability to bind to a moiety that localizes at or is local to a body site at which SOD therapy is desired, wherein amino acids 23 to 28 of the native sequence of Cu/Zn superoxide dismutase is modified as follows to include said tetrapeptide:

| Native Sequence: | $K^{23}E^{24}S^{25} N^{26}G^{27}P^{28}$ |
|---|---|
| Mutant Sequence: | $R^{23}G^{24}D^{25}$ — — $T^{26}$ | where - represents an amino acid deletion, said analog being SOD-AS-T-2 and having increased binding to a platelet.

2. A pharmaceutical composition for providing superoxide dismutase therapy comprising the analog of claim 1 admixed with a pharmaceutically acceptable parenteral vehicle.

3. DNA encoding the superoxide dismutase analog of claim 1.

4. An expression vector for expressing the DNA of claim 3 in an organism comprising the DNA of claim 17 operably connected to DNA that enables the expression of the DNA in the organism.

5. A host organism containing the vector of claim 4 which permits the expression of the analog by the organism.

6. A method of producing a superoxide dismutase analog having dismutase activity and whose amino acid sequence includes a heterologous peptide domain that provides the analog with an ability to bind to a moiety that localizes at or is local to a body site at which superoxide dismutase therapy is desired comprising growing the organism of claim 5 in a suitable growth medium under conditions that result in the expression of said DNA encoding the analog and production of said analog.

7. Superoxide dismutase analog SOD-AS-T-2.

* * * * *

UNITED STATES PATENT AND TRADEMARK OFFICE
CERTIFICATE OF CORRECTION

PATENT NO. : 5,171,680

DATED : December 15, 1992

INVENTOR(S) : G. Mullenbach et al.

It is certified that error appears in the above-identified patent and that said Letters Patent is hereby corrected as shown below:

Column 10,
In claim 4, line 2, "claim 17" should read --claim 3--.

Signed and Sealed this

Twenty-sixth Day of April, 1994

Attest:

BRUCE LEHMAN

Attesting Officer

Commissioner of Patents and Trademarks